United States Patent
Cartmell et al.

[11] Patent Number: 5,947,998
[45] Date of Patent: Sep. 7, 1999

[54] WOUND CLOSURE STRIPS AND PACKAGES THEREOF

[75] Inventors: James Vernon Cartmell, Xenia; Wayne Robert Sturtevant, Centerville; Albert Joseph Feczko, Middletown; Michael Lee Wolf, West Milton, all of Ohio

[73] Assignee: Technical Alternatives, Ltd., Centerville, Ohio

[21] Appl. No.: 08/940,870

[22] Filed: Sep. 30, 1997

[51] Int. Cl.$^6$ .................................................. A61B 17/06
[52] U.S. Cl. ........................ 606/213; 606/215; 206/441
[58] Field of Search ............................ 606/213, 215; 604/375; 206/440, 441, 447, 460; 428/8, 20, 41, 43; 602/46–58

[56] References Cited

U.S. PATENT DOCUMENTS

| | | |
|---|---|---|
| 1,911,291 | 5/1933 | Reynolds . |
| 2,880,862 | 4/1959 | Sermattei . |
| 3,143,208 | 8/1964 | Sizemore, Jr. . |
| 3,357,425 | 12/1967 | Morgan . |
| 3,402,716 | 9/1968 | Baxter . |
| 4,161,176 | 7/1979 | Harris, II et al. . |
| 4,392,898 | 7/1983 | Pithouse et al. . |
| 4,545,372 | 10/1985 | Lauritzen . |
| 4,549,653 | 10/1985 | Lauritzen . |
| 4,646,731 | 3/1987 | Brower . |
| 4,767,654 | 8/1988 | Riggsbee . |
| 4,837,062 | 6/1989 | Dunshee et al. . |
| 5,066,299 | 11/1991 | Bellingham . |
| 5,202,169 | 4/1993 | Spendlove . |
| 5,264,218 | 11/1993 | Rogozinski . |
| 5,520,629 | 5/1996 | Heinecke et al. . |

FOREIGN PATENT DOCUMENTS

| | | |
|---|---|---|
| 0 459 059 | 12/1991 | European Pat. Off. . |
| 2 165 759 | 4/1986 | United Kingdom . |
| WO 88 08690 | 11/1988 | WIPO . |

*Primary Examiner*—Michael Buiz
*Assistant Examiner*—Vikki Trinh
*Attorney, Agent, or Firm*—Killworth, Gottman, Hagan & Schaeff, L.L.P.

[57] ABSTRACT

Disclosed are wound closure strips which have an uniaxially oriented, silica filled, polyolefin substrate, a medical grade pressure sensitive adhesive, and a release sheet covering the pressure sensitive adhesive. Such strips are breathable, tearable to size, and may be removed from the skin with an alcohol wipe. Multiple wound closure strips are mounted on the upper surface of a backing sheet and pressure sensitive adhesive patch coated on the lower surface of the backing sheet, thereby making it possible to adhere the backing sheet to a surface near the intended point of use and, then, easily remove and handle the wound closure strips with a gloved hand. The wound closure strips may be color-coded and used not only for incisions and wounds but also for attaching catheters, and other medically related uses. Sterile packages of multiple wound closure strips make them useable in a sterile operation room arena.

13 Claims, 3 Drawing Sheets

WOUND CLOSURE STRIPS AND PACKAGES THEREOF

BACKGROUND OF THE INVENTION

The present invention relates to wound closure strips and, more specifically, it relates to sterilized packages of wound closure strips which are packaged in a manner which allows for easy handling by a gloved user and to wound closure strips which are easily torn to size.

Typically, wound closure strips are sold in either sterilized tape rolls or sterilized packages of elongated rectangular shaped strips. Rolls of tape become non-sterile after first usage. And yet tape rolls are often reused from patient to patient. In addition, after wound closure strips of various needed lengths are cut or torn from the tape roll they are often placed on non-sterile IV poles, surgical drapes or operating room tables and trays. Infection control specialists and epidemiologist are focusing of the infection potential from such procedures. Also, it is sometimes difficult to cut individual wound closure strips from tape rolls because cutting may cause the adhesive and, thus, the wound closure strip to adhere to the scissors and/or the gloves, making it difficult to cut and handle the strips. Accordingly, it is common practice to have an additional, ungloved, person in the operating room or emergency room to cut or tear off wound closure strips of appropriate lengths. That not only adds extra personnel usage but also contributes to the non-sterile handling of the wound closure strips.

Packages of wound closure strips present some of the some of the same problems. Typically, the packaged wound closure strips are mounted on backing cards with a number of wound closure strips (such as 4, 6 or 10) of the same length (such as 3, 4 or 5 inches) located in a side-by-side relationship on the backing card. Again, such strips most often are cut to size causing the adhesive and, thus, the wound closure strips to adhere to the scissors and/or the gloves.

Accordingly, it has been suggested that a package of wound closure strips of various lengths having rounded edges that are located in a side-by-side arrangement would allow a surgeon to estimate quickly what length of wound closure strip is necessary and then remove and place the sterile wound closure strip directly on the wound without having to cut or trim the wound closure strip. Thus, in Bellingham U.S. Pat. No. 5,066,299 there is disclosed a package having: a backing card (61), 2 transparent sheets (11) and (12) which seal the contents to keep the strips sterile until they are to be used, two lines of weakness (62) and (63) which are torn off so that the strips are more readily removable, and the strips which are spaced accordingly for ease of size recognition and selection for use (see FIGS. 1 and 5).

Other pre-pack arrangements are found for example in Morgan U.S. Pat. No. 3,357,425, which discloses a pressure sensitive adhesive sheet, pre-cut to a variety of shapes and sizes, for sequential application to a person's anatomy. The shapes are pre-cut to fit specific parts of the body, thereby allowing for a quick and proper wrap (see FIG. 1). In Lauritzen U.S. Pat. No. 4,545,372 there is disclosed a package adhesive bandage wherein the wrapping material, comprising a base portion (12) and cover portion (11), folds to enclose a length of bandage material (13). A line of weakness (15) separates the bandage from the wrapper while the edge of the cover portion (20) protrudes to form a pull tab for opening (see FIGS. 1 and 3). See also, Reynolds U.S. Pat. No. 1,911,291, which discloses a surgical dressing kit that provides for easy removal of bandage strips without the requirement of a cutting instrument. The kit includes a transverse slits (10) between the strips for ease of removal, a pad element (4) for the wound, and protecting strips (6) and (8) which cover the adhesive component (2) until the bandage is used (see FIGS. 1, 2 and 3). Finally in Harris U.S. Pat. No. 4,161,176, there is disclosed a color adaptable bandage wherein multiple layers of said bandage can be removed to approximate the user's skin color. The bandage (10) contains patches of film (20, 26 and 28) which can be incrementally removed to reveal a different color. However, none of the previously known packages of wound closure strips provide for affixing the package near the site of use for easily handling of the wound closure strips by a gloved user.

Accordingly, the need exists for even more convenient sterilized packages of wound closure strips for easy handling by a gloved user and for improved wound closure strips.

SUMMARY OF THE INVENTION

That need is met by the present invention which provides sterilized packages of wound closure strips which are packaged in a manner which allows for easy handling by a gloved user and provides would closure strips which are easily torn to size.

The wound closure strips of the present invention are easily torn to size because of the use of a unique substrate in their manufacture. That unique substrate is a silica filled polyolefin, preferably a polyethylene, which is breathable and which allows easy alcohol wipe removal from the skin. The wound closure strip is preferably of an elongated rectangular shape and the substrate is uniaxially oriented either longitudinally (for lengthwise tearing) or transversely (for tearing across the width) so as to render the wound closure strip tearable along the orientation. Scores, in the form of slits, notches, grooves, indents, or other tear starts may be formed in the ends of the substrate or in the elongated edges of the substrate to provide starts for the tear lines. A series of laterally offset scores may, thus, be formed at various points on the ends of the wound closure strip or along the elongated edges so that, in use, wound closure strips of the desired size may be made by tearing at the appropriate tear line. The wound closure strip has a medical grade pressure sensitive adhesive, preferably an acrylic adhesive, coated on one surface of the substrate. A releasable sheet is located adjacent the pressure sensitive adhesive. Thus, the wound closure strip may be a single strip having a releasable sheet which is sized to cover the pressure sensitive adhesive and which is removable, in whole or in part, in use.

Preferably, however, a plurality of wound closure strips are mounted on a backing sheet which has a release coating on it upper surface, the backing sheet becoming in that instance the releasable sheet. The releasable sheet or backing sheet may have at least one, and preferably two, lines of weakness formed therein, such as by kiss cutting, extending transversely to the elongation. The line(s) of weakness is/are positioned a distance from the end(s) of the wound closure strip(s) so that in use a portion of the releasable sheet or backing sheet remains with the wound closures strip at the end(s) after the rest of the releasable sheet is separated from the wound closure strip or the wound closure strip is removed from the backing sheet. That portion at one or both ends of the wound closure strip may be used as a non-adhesive gripping surface for handling the wound closure strip.

In one embodiment, the substrate is uniaxially oriented transversely to the elongation and there are scores on the elongated edges of the substrate for the wound closure strip aligned with the line(s) of weakness in the releasable sheet or backing sheet. Those enable easy tearing off of the non-adhesive gripping surface portion of the wound closure strip which has been used for handling purposes and throwing it away after the adhesive portion has been applied to the intended surface.

In another embodiment, the substrate is uniaxially oriented in the longitudinal direction, there are scores on the ends of the substrate, and there are longitudinal lines of weaknesses formed in the releaseable sheet or backing sheet aligned with those scores and extending to the transverse lines of weakness so as to permit lengthwise tearing of the wound closure strips and, then, removal of the releasable sheet or backing sheet at all but the ends so as to leave gripping surfaces, again for ease of handling by a gloved user. In this embodiment, the gripping surfaces may be pealed off at the time the wound closure strip is applied to the intended surface.

In that regard while the adhesive strips of the present invention are being referred to as wound closure strips that term is hereby defined as including other use of the strips such as to attach catheters, for application to CVP lines (IV hyperallimentation), for arterial lines, IV therapy and epidural trays, as well as for treating operative incision sites and in wound care.

When provided in package form, multiple wound closure strips will be releasably adhered to the upper surface of a backing sheet which has a release coating on that surface. The lower surface of the backing sheet, then, has a pressure sensitive adhesive thereon either as an overall coating or a partial coating and there is a removable release liner which covers that pressure sensitive adhesive. In use, the release liner is removed and the backing sheet is adhered to any desired surface near the point of use for the wound closures strips, i.e. on a surgical drape, operating room table or tray, etc. This allows for hands free removal of the wound closure strips from the backing sheet. A gloved user simply removes a wound closure strip using the gripping surface formed by the tear away portion(s) of the backing sheet as discussed above. Thereafter, the wound closure strip may be torn to size and the gripping surface and any excess portion of the strip discarded, all without any loss of sterility for the wound closure strip, or any danger of the strip adhering to gloves, scissors or any other unintended surface.

It is also possible to color code the wound closure strips by having strips of different colors with different intended uses in the same package or having different colored strips with a different intended use in separate packages so that the appropriate package of colored strips can be chosen for the use intended. For example, green strips could be used for intubation tubes and red for arterial lines to aid the anesthesiologist and to allow rapid localization of tubing.

Finally, the package of wound closure strips of the present invention is completed by placing one or more backing sheets upon which the wound closure strips are mounted in a sealed envelope and sterilizing the envelope and its contents. The envelope may be made of paper, plastic film, metal foil, or the combination thereof. Preferably the envelope is formed from one ply of a flexible transparent plastic film which permits the user to see the color coded wound closure strips, and another opaque ply which has informational printing thereon. Alternatively, informational labeling may be used on either ply. The two plays are, for example, heat sealed together to provide a sterile enclosure for the wound closure strips.

As can be seen, the present invention offers a product which provides sterility assurance for each individual use., wound closure strips that are packaged so that they can easily be handled by gloved users, adhesive strips that can be size tailored for specific use, strips that can be color coded, a product that can be placed in operating sterile field and a product that can be attached to a convenient site to allow hands free removal of the wound closure strips, all of which eliminates excessive waste of materials and unnecessary use of personnel.

In addition, the wound closure strips of the present invention are made with a unique substrate that is totally breathable, that can be accurately torn to any width or length, that allows for easy alcohol wipe removal from the skin, and that will adhere to moist skin, yet maintain a bacterial barrier, all in a product that can be manufactured without use of expensive roll manufacturing equipment.

Accordingly, it is an object of the present invention to provide an improved wound closure strip and to provide sterilized packages of such strips which are packaged in a manner which allows for easy handling by a gloved user.

These and other objects, features and advantages of the present invention will become apparent from the drawings, detailed description and claims.

DETAILED DESCRIPTION OF THE INVENTION

Figure 1:
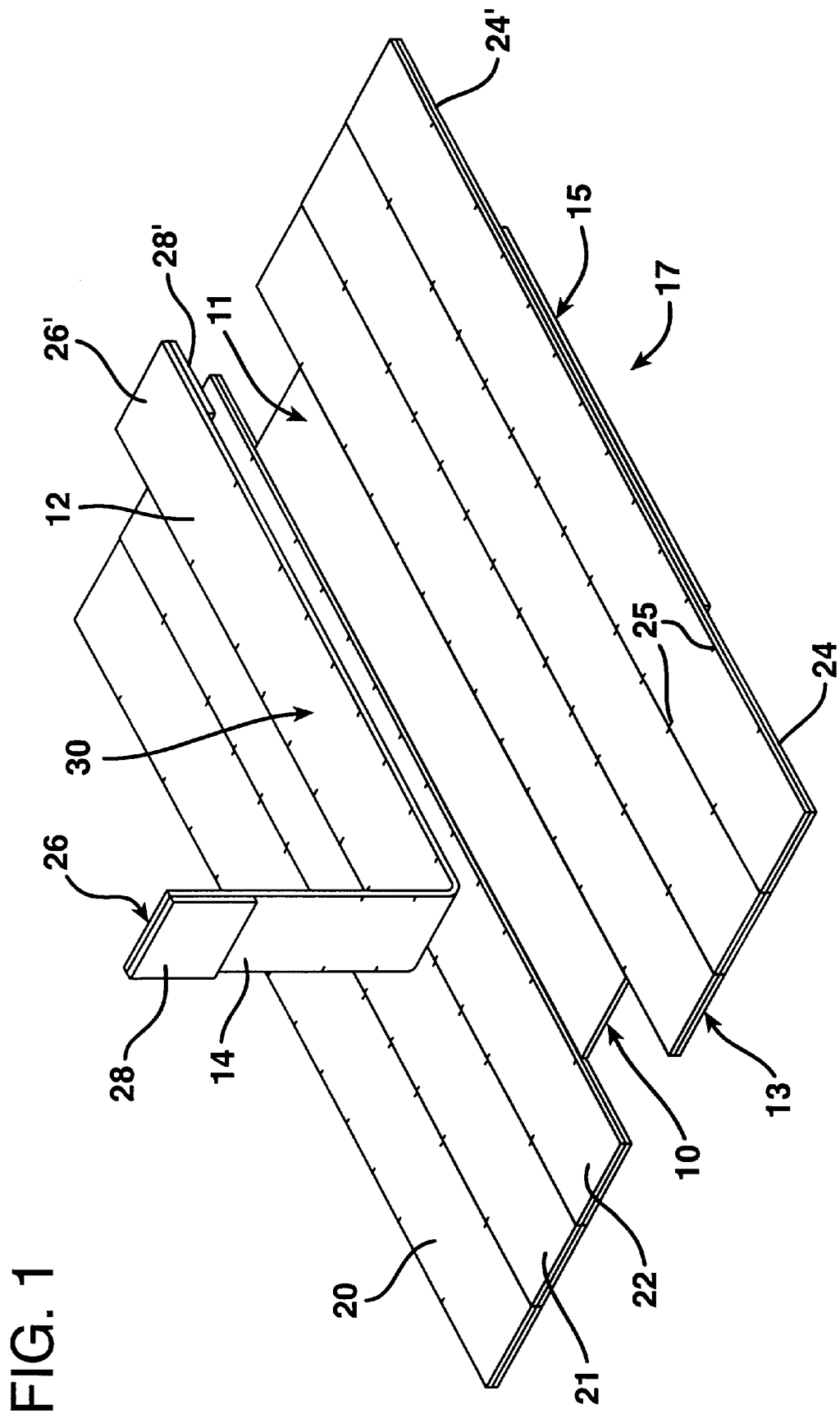
FIG. 1 shows multiple wound closure strips on a backing sheet.

Referring to FIG. 1, there is shown one embodiment of the present invention where a backing sheet 10 has multiple wound closure strips 20, 21, 22 etc. located in parallel, side-by-side relationship on backing sheet 10. Backing sheet 10 may be a paper sheet having a release coating such as a silicone coated on its upper surface 11. Wound closure strips 20, 21, 22 etc are formed from a substrate 12 made of a silica filled polyethylene material which may be Teslin (trademark) available from PPG Industries of Pittsburgh, Pa. Such a substrate material may be tinted or dyed a color so as to provide color-coded wound closure strips, either by way of different colored strips in the same package or different packages of colored strips. Such a substrate is also totally breathable which allows for adhesion to moist skin or diaphoretic skin, while maintaining a bacterial barrier. And yet, alcohol will seep through such a substrate so that if an alcohol soluble or partially alcohol soluble pressure sensitive adhesive is used, an alcohol wipe will permit removal of the wound closure strip from the skin without pulling hairs or damaging the skin.

Figure 2:
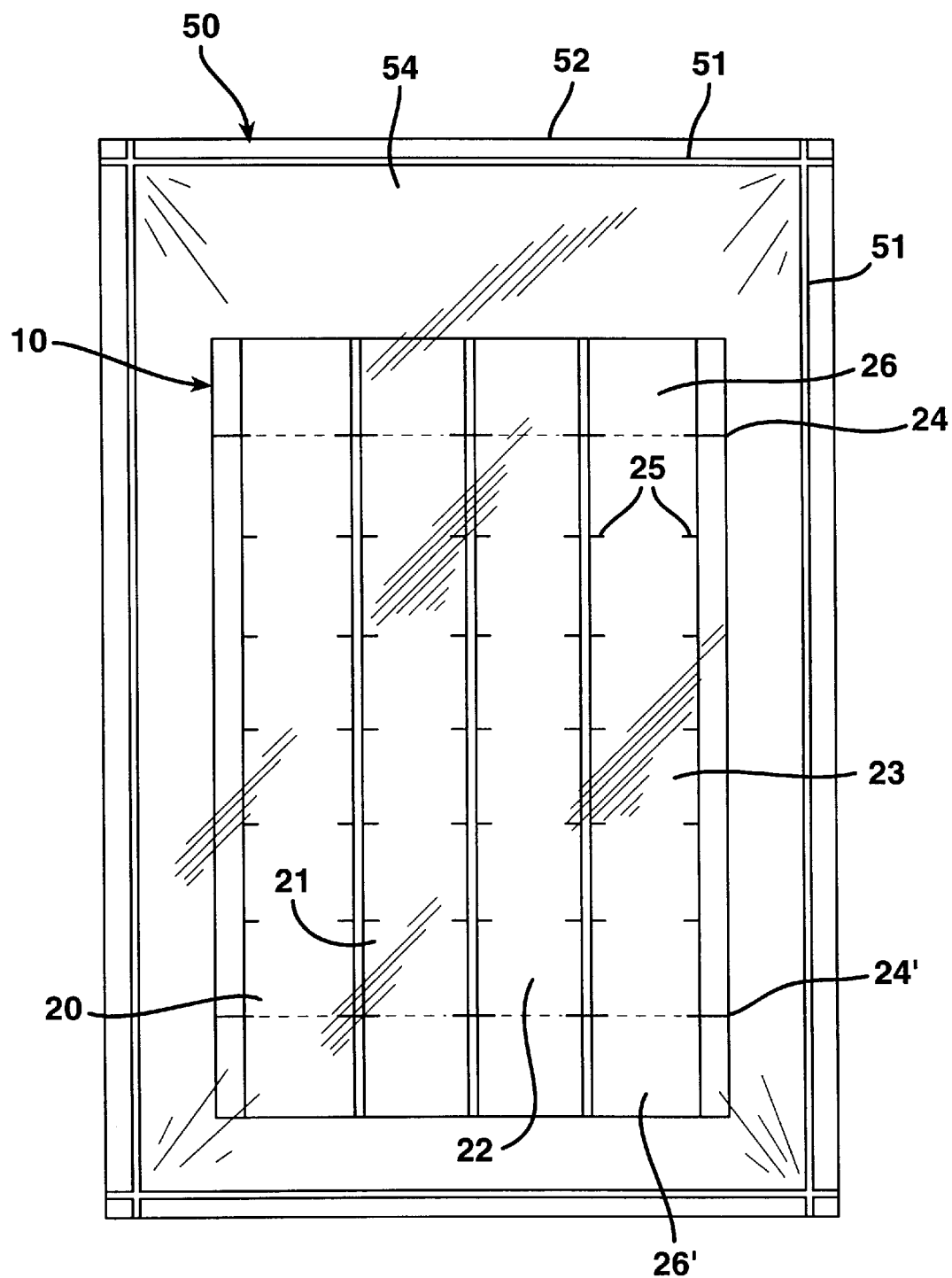
FIG. 2 shows a front view of a package of multiple wound closure strips of one embodiment of the present invention.

In FIGS. 1 and 2, substrate 12 has been uniaxially oriented and arranged such that the orientation runs transverse to the elongation (i.e. across the narrower width). Scores 25, in the form of slits which have been kiss cut into substrate 12, are located on the elongated edges of each wound closure strip 20, 21, and 22 etc. Those scores are used as starts for a tear line along the orientation (i.e. across the narrow width of the wound closure strip). That permits easy tearing of the wound closure strip in use so that it is of an appropriate length for use.

Figure 3:
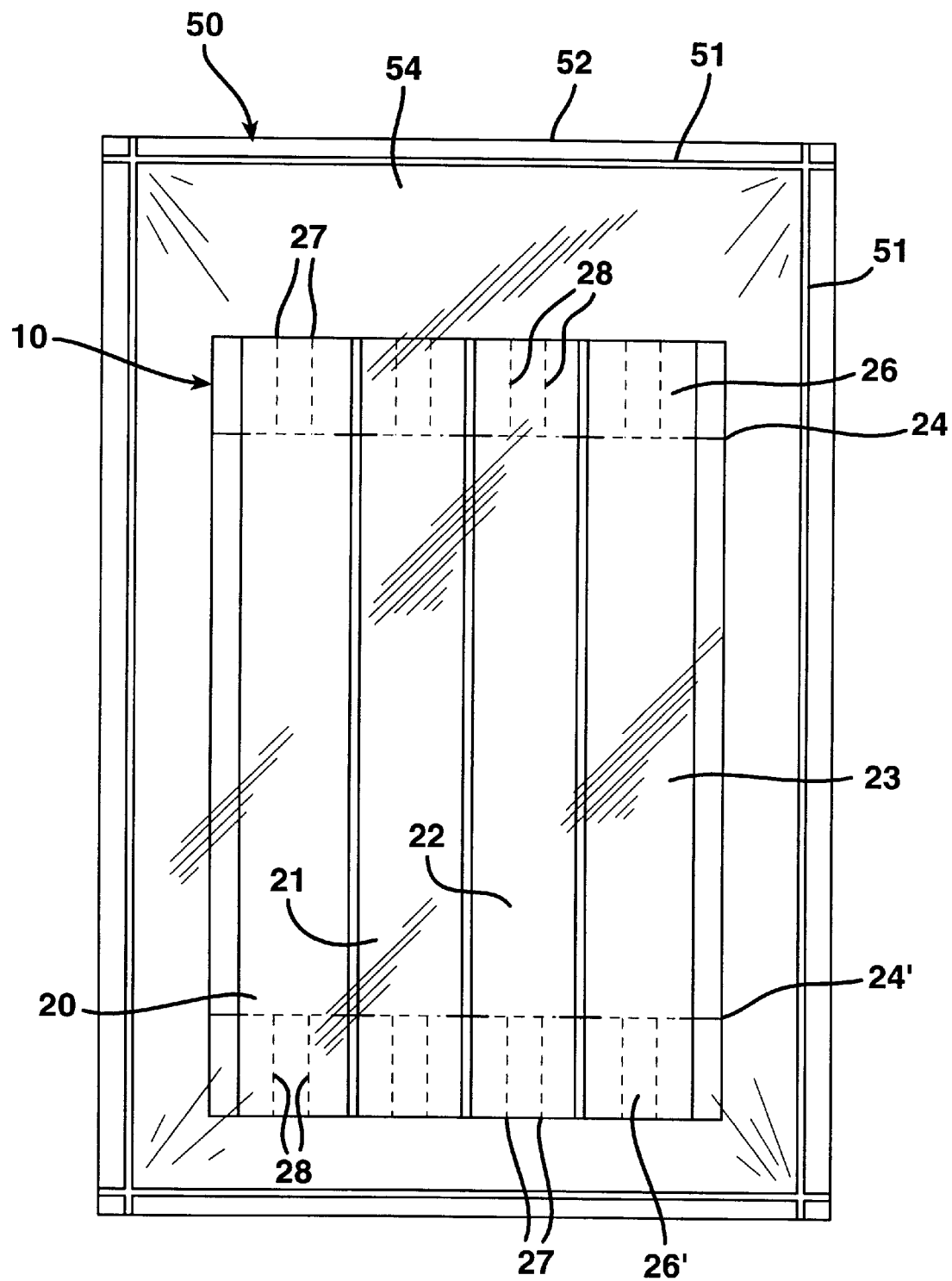
FIG. 3 shows a front view of a package of multiple wound closure strips of another embodiment of the present invention.

In FIG. 3, substrate 12 has been uniaxially oriented and arranged such that the orientation runs parallel to the elongation (i.e., longitudinally along the length of the strip.) Scores 27, in the form of slits which have been kiss cut into substrate 12, are located on the ends of each wound closure strip 20, 21, 22, etc. That permits easy tearing of the wound closure strip in use so that it is of an appropriate width for use. For that purpose, longitudinal lines of weakness 28 are formed in the backing sheet 10 aligned with scores 27 and extending to transverse lines of weakness 24, 24', so that the gripping surface(s) of the backing sheet can also be easily torn.

Thus as shown in FIGS. 1, 2 and 3 backing sheet 10 has transverse lines of weakness 24, 24' formed in it such as by kiss cutting a slit therein or using embossing/cutting rollers to form a sufficient indentation therein such that portions 28 and 28' are easily separated from the rest of backing sheet 10 and upon removal of a wound closure strip, ends 26, 26' of the wound closure strip have portions 28,28' of the backing sheet thereon. Those ends 26, 26' of the wound closure strip may be used as a non-adhesive gripping surface for handling of the wound closure strip.

The remaining portion of the wound closure strip will have a pressure sensitive adhesive 14 exposed so that the wound closure strip may be applied (after tearing to size, removing ends 26, 26' and/or portions 28, 28' of the backing sheet, or both) to the intended surface whether it be for the purpose of wound or incision closure or for the purpose of attaching catheters, IV tubes, etc. Pressure sensitive adhesive 14 may be a medical grade acrylic such as Gelva 737 from Monsanto Co. of St. Louis, Mo. or Duro Tak 80-2434 from National Starch and Chemical Co. of Bridgewater, N.J. Any other equivalent medical grade pressure sensitive adhesive may be used.

As also shown in FIG. 1, the lower surface 13 of backing sheet 10 has a pressure sensitive adhesive 15 coated on it. As shown, pressure sensitive adhesive 15 only partially covers lower surface 13 (i.e. forms a rectangular patch thereon); although, it may be an essentially complete coating or a patterned coating. Pressure sensitive adhesive 15 may be a medical grade adhesive such as that used for pressure sensitive adhesive 14, but it need not be since pressure sensitive adhesive 15 is not intended to be applied to the skin. Thus pressure sensitive adhesive 15 may be an acrylic or a rubber based adhesive. Upon removal of release liner 17, which may be a silicone coated paper, pressure sensitive adhesive 15 is used to attach backing sheet 10 to a surface, such as an operating room drape, tray, table, etc., near the location of use for the wound closure strips. Since backing sheet 10 is then held family in place, and since it has lines of weakness 24, 24' formed therein, a gloved user, such as operating or emergency room personnel, can easily remove a wound closure strip from backing sheet 10 as shown by numeral 30 and then handle it as described previously.

The assembly shown in FIGS. 1, 2 and 3 can easily be manufactured without expensive roll manufacturing equipment. Thus sheets or webs of backing sheet paper are coated with a release coating on the upper surface thereof and pattern or spot coated with a pressure sensitive adhesive on the lower surface thereof. A corresponding sheet or web of Teslin substrate which has a medical grade acrylic adhesive coated on one of its surfaces is laminated to the backing sheet paper with the pressure sensitive adhesive layer next to the release coating on the backing sheet paper. Alternatively, the medical grade pressure sensitive adhesive can be coated over the release coating on the backing sheet paper, and the Teslin substrate laminated to it. At the same time a release liner is laminated over the pressure sensitive adhesive on the lower surface of the backing sheet paper. Slits are then kiss cut into the Teslin substrate to form a series of elongated wound closure strips and offset scores are formed by either cross-cutting along the thus formed elongated edges of the wound closure strips or by partially cutting the ends of wound closure strips at the same time the full elongated slits are formed. At the same time transverse lines of weakness are formed in the backing sheet paper by kiss cutting it from the underside at distances from the ends of the elongated wound closure strips which preferably align with the first set of scores inwardly from those ends. In the FIG. 3 embodiment, the longitudinal lines of weakness are formed at the same time and in the same manner. Thereafter the sheets or webs are cut to size, if need be, to form a backing sheet 10 having the desired number of wound closure strips 20, 21, 22 etc. of the appropriate width and length mounted thereon.

FIGS. 2 and 3, where like numerals are used, show packages 50 of wound closure strips. Package 50 has an envelope made up of lower ply 52 and upper ply 54 which plies are sealed together at the periphery 51 of the package 50. Lower ply 52 is preferably opaque and may be formed of paper, plastic film, metal foil, or the combination thereof. Preferably it is a glassine paper or synthetic paper, such as Tyvek from E. I. DuPont de Namours of Wilmington, Del., which is a printable material such that information may be printed on lower ply 52. Upper ply 54 may also be a paper, plastic film, metal foil or combination thereof. Preferably it is a transparent plastic film such as low density polyethylene. Informational labels may be attached to upper ply 54 as desired. Periphery 51 is sealed by heat sealing lower ply 52 and upper ply 54 together or they are sealed by use of a sealing adhesive between plies 52 and 54 at the periphery followed by pressure application. Preferably the seal is a pealable one so that upper ply 54 can be pealed from lower ply 52 and backing sheet 10 having wound closure strips 20, 21, 22, and 23 thereon removed from package 50.

Sterilization of package 50 and its contents can be accomplished by exposure to ethylene oxide or by gamma irradiation after sealing the package or by other known sterilization techniques used for paper and plastic products.

As such, a sterile package is provided for each use and it may be used in the sterile operating room arena. Further because the packages may contain different numbers of wound closure strips, proper selection of the package or packages needed for a particular use means that there is little waste to be dealt with.

From the above disclosure of the general principles of the present invention and the preceding detailed description, those skilled in this art will readily comprehend the various modifications to which the present invention is susceptible. Therefore, the scope of the invention should be limited only by the following claims and equivalents thereof.

What is claimed:

1. A package of wound closure strips for easy handling by a gloved user comprising:

a backing sheet for supporting multiple wound closure strips, said backing sheet having an upper surface and a lower surface and having a release coating on said upper surface, said backing sheet further having a first pressure sensitive adhesive coated on at least a portion of said lower surface, multiple wound closure strips releasably mounted on said upper surface of said backing sheet by use of a second pressure sensitive adhesive between said wound closure strips and said release coating on said upper surface of said backing sheet, a removable release liner covering said first pressure sensitive adhesive coated on at least a portion of said lower surface of said backing sheet, whereby in use said release liner may be removed and said backing sheet with said wound closure strips mounted thereon adhered with said first pressure sensitive adhesive to a surface at the area of use, a sealed envelope containing one or more of said backing sheets having said wound closure strips mounted thereon.

2. The package of claim 1 wherein said multiple wound closure strips have an elongated rectangular shape and are mounted on said upper surface of said backing sheet side-by-side.

3. The package of claim 2 wherein said multiple wound closure strips are uniaxially oriented transversely to the elongation so as to be tearable along the orientation across the width of said strips.

4. The package of claim 3 wherein said multiple wound closure strips are scored at locations along the elongated edges thereof to provide a starts for tear lines.

5. The package of claim 2 wherein said wound closure strips are uniaxially oriented parallel to the elongation so as to be tearable along the orientation along the length of said strips.

6. The package of claim 5 wherein said wound closure strips are scored at locations at the ends thereof to provide starts for the tear lines.

7. The package of claim 2 wherein said backing sheet has a line of weakness extending along said backing sheet at a location positioned a distance from where at least one end of said multiple wound closure strips is located on said backing sheet, whereby when the user removes a wound closure strip from said backing sheet the portion of said backing sheet at said at least one end is removed with the wound closure strip so as to provide a non-adhesive gripping surface for handling the wound closure strip.

8. The package of claim 7 wherein two lines of weakness are formed in said backing sheet, each at a location positioned a distance from where the ends of said multiple wound closure strips are located on said backing sheet whereby when the user removes a wound closure strip from said backing sheet the portions of said backing sheet at each end of the multiple closure strip is removed with the wound closure strip to provide two non-adhesive gripping surfaces for handling the wound closure strip.

9. The package of claim 1 wherein said multiple wound closure strips are formed from a silica filled polyolefin substrate and said second pressure sensitive adhesive is a medical grade acrylic pressure sensitive adhesive.

10. The package of claim 1 wherein said envelope and its contents have been sterilized.

11. The package of claim 10 wherein said envelope is made of a material selected from the group consisting of paper, plastic film, metal foil, and the combination thereof.

12. The package of claim 1 wherein said multiple wound closure strips are color coded.

13. The package of claim 12 wherein ones of said multiple wound closure strips in said package have a color different from other ones of said multiple wound closure strips in said package.

\* \* \* \* \*